(12) United States Patent
Ladet et al.

(10) Patent No.: US 8,829,071 B2
(45) Date of Patent: Sep. 9, 2014

(54) MEDICAL DEVICE WITH DEGRADATION-RETARDING COATING

(75) Inventors: Sébastien Ladet, Lyons (FR); Philippe Gravagna, Irigny (FR)

(73) Assignee: Sofradim Production (FR)

( * ) Notice: Subject to any disclaimer, the term of this patent is extended or adjusted under 35 U.S.C. 154(b) by 268 days.

(21) Appl. No.: 13/120,674

(22) PCT Filed: Feb. 22, 2010

(86) PCT No.: PCT/IB2010/000571
§ 371 (c)(1),
(2), (4) Date: Dec. 8, 2011

(87) PCT Pub. No.: WO2010/095044
PCT Pub. Date: Aug. 26, 2010

(65) Prior Publication Data
US 2012/0071974 A1   Mar. 22, 2012

Related U.S. Application Data

(60) Provisional application No. 61/154,365, filed on Feb. 21, 2009.

(51) Int. Cl.
| | | |
|---|---|---|
| C09D 105/08 | (2006.01) | |
| C08L 101/16 | (2006.01) | |
| A61L 17/06 | (2006.01) | |
| C08J 7/04 | (2006.01) | |
| A61L 17/14 | (2006.01) | |

(52) U.S. Cl.
CPC .............. *A61L 17/145* (2013.01); *C09D 105/08* (2013.01); *C08J 7/047* (2013.01); *A61L 17/06* (2013.01)
USPC ........................... 523/113; 427/2.1; 623/11.11

(58) Field of Classification Search
None
See application file for complete search history.

(56) References Cited

U.S. PATENT DOCUMENTS

| | | | | |
|---|---|---|---|---|
| 4,326,532 A | * | 4/1982 | Hammar | 604/266 |
| 4,931,546 A | * | 6/1990 | Tardy et al. | 530/356 |
| 5,525,348 A | * | 6/1996 | Whitbourne et al. | 424/423 |
| 5,804,318 A | * | 9/1998 | Pinchuk et al. | 428/421 |
| 6,107,453 A | * | 8/2000 | Zuccato et al. | 528/481 |
| 6,238,799 B1 | * | 5/2001 | Opolski | 428/423.1 |
| 6,342,591 B1 | * | 1/2002 | Zamora et al. | 536/21 |
| 6,461,665 B1 | * | 10/2002 | Scholander | 427/2.24 |
| 6,559,132 B1 | * | 5/2003 | Holmer | 514/56 |
| 6,767,405 B2 | * | 7/2004 | Eketorp et al. | 118/411 |
| 2006/0036022 A1 | * | 2/2006 | Callaghan et al. | 524/555 |
| 2009/0018646 A1 | * | 1/2009 | Zhao | 623/1.43 |

FOREIGN PATENT DOCUMENTS

| | | | |
|---|---|---|---|
| BE | 1 008 260 A6 | 2/1996 | |
| EP | 1 790 702 A1 | 5/2007 | |
| EP | 1 795 563 A1 | 6/2007 | |
| EP | 2 014 308 A2 | 1/2009 | |
| EP | 2014308 A2 * | 1/2009 | A61K 47/48 |
| WO | WO 2007/121055 | 10/2007 | |
| WO | WO 2007121055 A1 * | 10/2007 | C08G 63/66 |

OTHER PUBLICATIONS

International Search Report PCT/IB2010/000571 dated Sep. 3, 2010.

\* cited by examiner

*Primary Examiner* — James J Seidleck
*Assistant Examiner* — Peter A Salamon

(57) ABSTRACT

The present disclosure relates to implantable bioabsorbable medical devices having an amphiphilic coating for delaying the degradation of the device and methods of making such devices.

20 Claims, 3 Drawing Sheets

US 8,829,071 B2

MEDICAL DEVICE WITH DEGRADATION-RETARDING COATING

CROSS-REFERENCE TO RELATED APPLICATIONS

This application is a U.S. National Stage Application filed under 35 U.S.C. §371(a) of International Application No. PCT/IB2010/000571, filed Feb. 22, 2010, which claims the benefit of and priority to U.S. Provisional Patent Application Ser. No. 61/154,365 filed Feb. 21, 2009, the entire contents of which are incorporated by reference herein.

BACKGROUND

1. Technical Field

The present disclosure relates to methods of making implantable medical devices having a coating that delays degradation of the implantable medical device.

2. Background of Related Art

Implantable medical devices are formed from a variety of different biodegradable and non-biodegradable materials. Non-biodegradable devices offer increased strength and support however, the permanency of these devices may prevent cellular growth, thereby inhibiting integration of the device. Biodegradable devices are designed to degrade (hydrolytically or enzymatically) within the body providing opportunity for cellular ingrowth and integration. Immediate degradation of the device may, however, initiate an immune response and inflammation of the tissue which in turn speeds degradation of the device. This can potentially weaken the device before in-growing cells and newly formed tissue are strong enough to replace the device.

Accordingly, it would be beneficial to provide a medical device which includes a coating that slows the degradation process of the device, thereby improving in vivo persistence of the device while also increasing the ability of the device to promote cellular in growth and integration.

SUMMARY

A first aspect of the present invention relates to a medical device comprising
 a bioabsorbable polymeric substrate having a coating, the coating comprising an amphiphilic compound having a hydrophilic portion and a hydrophobic portion, the hydrophobic portion of the amphiphilic compound being covalently bonded to the bioabsorbable polymeric substrate.

In the present application, the term "bioresorbable" is intended to mean the characteristic according to which a substrate and/or a material is resorbed by the biological tissues and the surrounding fluids and disappears in vivo after a given period of time, that may vary, for example, from one day to several months, depending on the chemical nature of the substrate and/or of the material.

Another aspect of the invention relates to a method of increasing the degradation time of a bioabsorbable medical device, the method comprising:
 providing a coating on the medical device by reacting 1) a bioabsorbable polymeric substrate functionalized with a first reactive member with 2) an amphiphilic compound having a hydrophobic portion and a hydrophilic portion, the hydrophobic portion including a second, complementary reactive member.

Another aspect of the invention relates to a method of providing a medical device with an amphiphilic coating comprising functionalizing at least a portion of the medical device with a first reactive member and reacting the functionalized portion of the medical device with an amphiphilic compound having a hydrophobic portion and a hydrophilic portion, the hydrophobic portion including a second reactive member that is complementary to the first reactive member.

In embodiments, the surface of the bioabsorbable substrate has a first reactive member attached thereto and the hydrophobic portion of the amphiphilic compound has a second reactive member attached thereto, said first reactive member and second reactive member being able to specifically interact together to covalently bond the hydrophobic portion of the amphiphilic compound to the bioabsorbable polymeric substrate.

In the present application, the expressions "has attached thereto", "is functionalized", "includes" applied to the polymeric bioabsorbable device or the amphiphilic compound, in particular its hydrophobic portion, in relation with a reactive member or a functionality are used interchangeably to mean that the polymeric bioabsorbable device, the amphiphilic compound, in particular its hydrophobic portion, include said reactive member or functionality.

In embodiments, the first reactive member is a nucleophilic functional group and the second reactive member is an electrophilic functional group.

In other embodiments, said first and second reactive members are able to interact together according to a reaction selected from the group consisting in Huisgen cycloaddition, Diels-Alder reactions, thiol-alkene reactions and maleimide-thiol reactions.

For example, the first reactive member is an alkyne and the second reactive member is an azide. Alternatively, the first reactive member may be an azide and the second reactive member may be an alkyne.

In other embodiments, the first reactive member is an azide and the second reactive member is an alkene.

In embodiments, the hydrophilic portion is derived from a chitosan oligomer having a low degree of acetylation, ranging from about 0 to about 30%, and the hydrophobic portion is derived from a chitosan oligomer having a higher degree of acetylation, greater than about 50% at a pH<6.

In other embodiments, the hydrophobic portion is derived from a chitosan oligomer having a low degree of acetylation, ranging from about 0 to about 10%, and the hydrophilic portion is derived from a hyaluronic acid oligomer or alginate oligomer which under pH>7 conditions displays a negative charge.

Implantable medical devices are described herein which include a bioabsorbable polymeric substrate having a surface to which a degradation-retarding coating is attached. The degradation-retarding coating includes an amphiphilic compound—that is, a compound having a hydrophilic portion and a hydrophobic portion. The hydrophobic portion of the amphiphilic compound is functionalized with a reactive member that reacts with a reactive member on a functionalized surface of the bioabsorbable polymeric substrate. In this manner, the hydrophobic portion of the amphiphilic compound is covalently bound to a surface of the implantable medical device.

Methods of making such medical devices are described herein which include reacting a functionalized surface of the bioabsorbable polymeric substrate with an amphiphilic compound having a functionalized hydrophobic portion. In embodiments, the surface of the bioabsorbable polymeric substrate and the hydrophobic portion of the amphiphilic compound are functionalized with reactive members involved in click chemistry.

DETAILED DESCRIPTION OF PREFERRED EMBODIMENTS

Implantable medical devices in accordance with the present disclosure include a bioabsorbable polymeric substrate having a surface to which a degradation-retarding coating containing an amphiphilic compound is covalently bound. At least a portion of a surface of the bioabsorbable polymeric substrate is functionalized with a first reactive member and the hydrophobic portion of the amphiphilic compound is functionalized with a second reactive member that is reactive with the first reactive member on the surface of the bioabsorbable polymeric substrate. The first and second reactive members react to covalently bond the hydrophobic portion of the amphiphilic compound to the surface of the bioabsorbable polymeric substrate.

Figure 1:
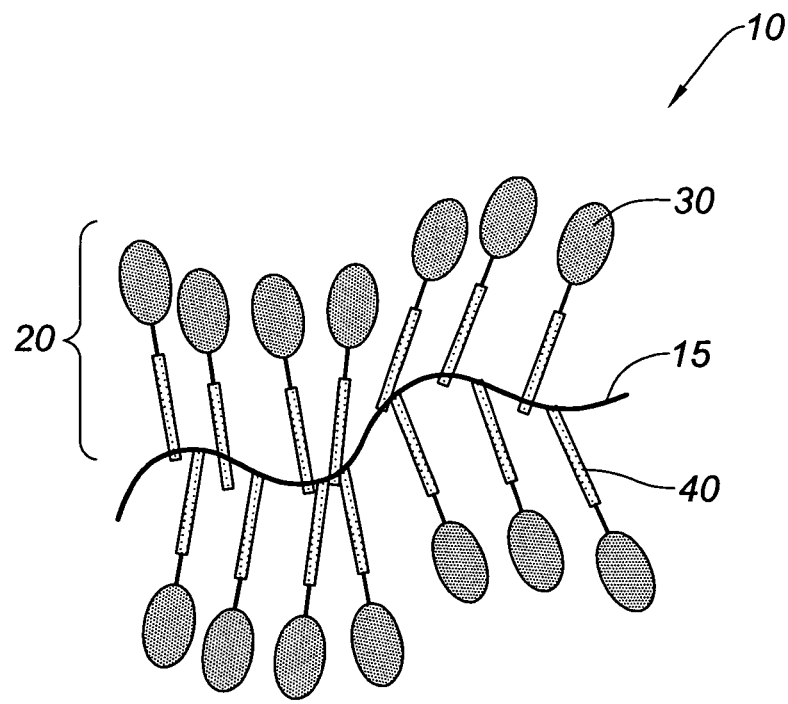
FIG. 1 schematically illustrates a medical device in accordance with an embodiment described herein.

Turning now to FIG. 1, medical device 10, has a bioabsorbable polymeric substrate shown as a single fiber or monofilament 15 having coating 20 that includes an amphiphilic compound having hydrophilic portion 30 and hydrophobic portion 40 wherein hydrophobic portion 40 is covalently attached to substrate 15. Hydrophilic portion 30 of amphiphilic coating 20 is positioned away from substrate 15 and provides an environment favorable for cellular attachment and infiltration. Hydrophobic portion 40 is positioned nearest substrate 15 and provides a barrier preventing water diffusion and also cell attraction to substrate 15, thereby retarding the degradation of medical device 10 and increasing the in vivo persistence of medical device 10.

Figure 2:
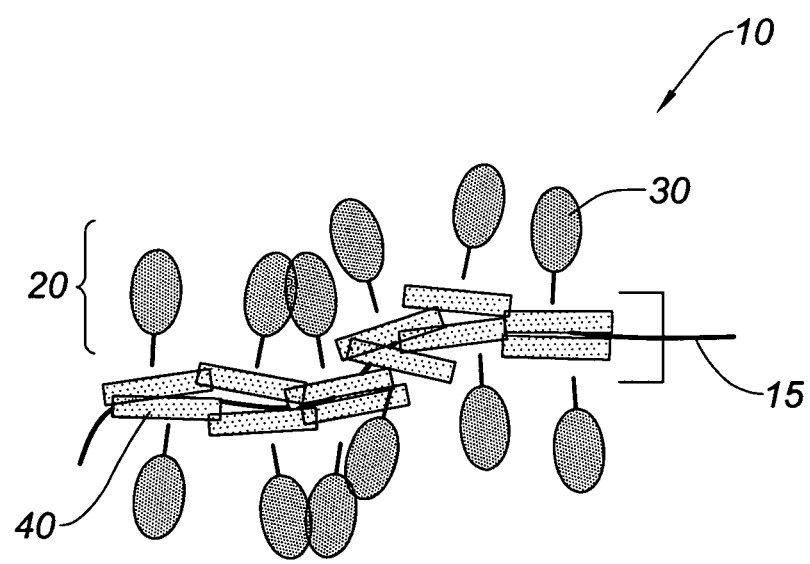
FIG. 2 schematically illustrates the effect of implantation on the embodiment of FIG. 1.

As shown in FIG. 2, hydrophobic portion 40 of amphiphilic compound 20 collapses along the surface of substrate 15 following implantation and prevents cellular migration during the early stages of the healing process and thereby reducing any inflammatory response. By limiting the inflammatory response during the early phases of the healing process, the long term performance of the implant is improved.

The Polymeric Substrate

The substrate of the medical devices described herein may be made from any biodegradable polymer. The biodegradable polymer may be a homopolymer or a copolymer, including random copolymer, block copolymer, or graft copolymer. The biodegradable polymer may be a linear polymer, a branched polymer, or a dendrimer. The biodegradable polymers may be of natural or synthetic origin. Examples of suitable biodegradable polymers include, but are not limited to polymers such as those made from lactide, glycolide, caprolactone, valerolactone, carbonates (e.g., trimethylene carbonate, tetramethylene carbonate, and the like), dioxanones (e.g., 1,4-dioxanone), δ-valerolactone, 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly(ortho esters), hydroxy alkanoates, tyrosine carbonates, polyimide carbonates, polyimino carbonates such as poly (bisphenol A-iminocarbonate) and poly(hydroquinone-iminocarbonate), polyurethanes, polyanhydrides, polymer drugs (e.g., polydiflunisol, polyaspirin, and protein therapeutics) and copolymers and combinations thereof. Suitable natural biodegradable polymers include those made from collagen, chitin, chitosan, cellulose, poly(amino acids), polysaccharides, hyaluronic acid, gut, copolymers and derivatives and combinations thereof.

The bioabsorbable polymeric substrate may be fabricated into any desired physical form. The polymeric substrate may be fabricated for example, by spinning, casting, molding or any other fabrication technique known to those skilled in the art. The polymeric substrate may be made into any shape, such as, for example, a fiber, sheet, rod, staple, clip, needle, tube, foam, or any other configuration suitable for a medical device. Where the polymeric substrate is in the form of a fiber, the fiber may be formed into a textile using any known technique including, but not limited to, knitting, weaving, tatting and the like. It is further contemplated that the polymeric substrate may be a non-woven fibrous structure.

The present bioabsorbable polymeric substrate having a coating containing an amphiphilic compound may be used as any medical device suitable for implantation. Some non-limiting examples include monofilaments, multifilaments, surgical meshes, ligatures, sutures, staples, patches, slings, foams, pellicles, films, barriers, and the like.

The Amphiphilic Compound

The amphiphilic compound includes at least one portion which is hydrophilic and at least one portion which is hydrophobic. The terms "hydrophilic" and "hydrophobic" are generally defined in terms of a partition coefficient P, which is the ratio of the equilibrium concentration of a compound in an organic phase to that in an aqueous phase. A hydrophilic compound has a log P value less than 1.0, typically less than about −0.5, where P is the partition coefficient of the compound between octanol and water, while hydrophobic compounds will generally have a log P greater than about 3.0, typically greater than about 5.0.

The amphiphilic compound may be linear, branched, block or graft copolymers. The hydrophilic portions are derived from hydrophilic polymers or compounds selected from the member consisting of polyamides, hydrophilic polyurethanes, polylactones, polyimides, polylactams, poly-vinyl-pyrrolidone, polyvinyl alcohols, polyacrylic acid, polymethacrylic acid, poly(hydroxyethyl methacrylate), gelatin, dextran, oligosaccharides, such as chitosan, hyaluronic acid, alginate, chondroitin, mixtures and combinations thereof. The hydrophobic portions are derived from hydrophobic polymers or compounds selected from the member consisting of polyethylene, polypropylene, hydrophobic polyurethanes, polyacrylates, polymethacrylates, fluoropolymers, polycaprolactone, polylactide, polyglycolide, phospholipids, and polyureas, poly(ethylene/-vinyl acetate), polyvinylchloride, polyesters, polyamides, polycarbonate, polystyrenes, polytetrafluoroethylene, silicones, siloxanes, fatty acids, and chitosan having high degrees of acetylation and mixtures and combinations thereof. The amphiphilic compound may include any biocompatible combination of hydrophilic and hydrophobic portions.

In embodiments, the amphiphilic compound may include a hydrophobic portion derived from a fatty acid, some non-limiting examples include saturated fatty acids, monoenoic fatty acids, polyenoic fatty acids, methylene-interrupted polymethylene-interrupted, conjugated, allenic acids, cumulenic acids, acetylenic fatty acids, hydroxy fatty acids, dicarboxylic acids, fatty acid carbonates, divinyl ether fatty acids, sulfur containing fatty acids, fatty acid amides, methoxy and acetoxy fatty acids, keto fatty acids, aldehydic fatty acids, halogenated fatty acids (F, Cl, Br), nitrated fatty acids, arsenic containing fatty acids, branched-chain fatty acids, mono or multibranched chain fatty acids, branched methoxy fatty acids, branched hydroxy fatty acids, ring containing fatty acids, cyclopropane acids, cyclobutane acids, cyclopentenyl acids, furanoid acids, cyclohexyl acids, phenylalkanoic acids, epoxy acids, cyclic fatty peroxides, lipoic acids and combinations thereof. Examples of saturated fatty acids include butanoic, pentanoic, hexanoic, octanoic, nonanoic, decanoic, dodecanoic, tetradecanoic, hexadecanoic, heptadecanoic, octadecanoic, eicosanoic, docosanoic, tetracosanoic, hexacosanoic, heptacosanoic, and octacosanoic. In embodiments, the fatty acid may include one of the following formulas: $C_6H_{11}O$, $C_{10}H_{19}O$, $C_{16}H_{31}O$, $C_{22}H_{43}O$. The amphiphilic compound may also include a hydrophilic portion derived from an oligosaccharide such as chitosan, hyaluronic acid, alginates or chondroitin sulfate.

Chitosan is a natural polysaccharide comprising copolymers of glucosamine and N-acetylglucosamine, and can be obtained by the partial acetylation of chitin, from any source (e.g., crustacean shells, squid pen, and mushrooms), the second most abundant natural polymer after cellulose. The process of acetylation involves the removal of acetyl groups from the molecular chain of chitin, leaving behind a complete amino group ($-NH_2$) and chitosan versatility depends mainly on this high degree chemical reactive amino groups. As the degree of acetylation increases, the more hydrophobic the chitosan becomes. Conversely, as the degree of acetylation decreases, the more hydrophilic the chitosan becomes under a pH<6. Thus, in some embodiments, chitosan oligmers displaying different degrees of acetylation may be combined to form an amphiphilic compound. Moreover, in some embodiments in which more than one oligosaccharide may be utilized to form the amphiphilic compound, the degree of acetylation of the chitosan oligomers may be altered depending on the hydrophilicity of the other oligosaccharides. For instance, the amphiphilic compound may include a hydrophilic portion derived from a chitosan oligomer having a low degree of acetylation, ranging from about 0 to about 30%, and a hydrophobic portion derived from a chitosan oligomer having a higher degree of acetylation, greater than about 50% at a pH<6. Alternatively, the amphiphilic compound may be formed under a raised pH (pH>7) such that the compound includes a hydrophobic portion derived from a chitosan oligomer having a low degree of acetylation, ranging from about 0 to about 10%, and a hydrophilic portion derived from a hyaluronic acid oligomer or alginate oligomer which under the raised pH conditions displays a negative charge. Under the raised pH conditions, the chitosan oligomer having a low degree of acetylation displays a positive charge and becomes more hydrophilic.

In still other embodiments, a fatty acid hydrophobic portion may be combined with a hydrophilic drug. Some non-limiting examples of hydrophilic drugs include oxytocin, vasopressin, adrenocorticotrophic hormone (ACTH), epidermal growth factor (EGF), transforming growth factor antagonists, prolactin, luliberin or luteinizing hormone releasing hormone (LH-RH), LH-RH agonists or antagonists, growth hormone, growth hormone releasing factor, insulin, somatostatin, bombesin antagonists, glucagon, interferon, gastrin, tetragastrin, pentagastrin, urogastrone, secretin, calcitonin, enkephalins, endorphins, angiotensins, renin, bradykinin, bacitracins, polymyzins, colistins, tyrocidin, gramicidines, and synthetic analogues and modifications and pharmaceutically-active fragments thereof, monoclonal antibodies and soluble vaccines.

Coating the Polymer Substrate with the Amphiphilic Compound

In order to covalently bond the amphiphilic compound to the surface of the bioabsorbable polymeric substrate, the surface of the bioabsorbable polymeric substrate is functionalized with a first reactive member and the hydrophobic portion of the amphiphilic compound is functionalized with a second reactive member. The first and second reactive members are complementary. By "complementary" it is meant that the first and second reactive members are able to specifically interact together to covalently bond the amphiphilic compound to the functionalized polymeric substrate.

In embodiments, the surface of the bioabsorbable polymeric substrate and the hydrophobic portion of the amphiphilic compound are functionalized with electrophilic or nucleophilic functional groups, such that, for example, a nucleophilic functional group on the surface of the bioabsorbable polymeric substrate may react with an electrophilic functional group on the hydrophobic portion of the amphiphilic compound to form a covalent bond.

Virtually any nucleophilic group can be used to functionalize the surface of the bioabsorbable polymeric substrate, so long as reaction can occur with the electrophilic group on the hydrophobic portion of the amphiphilic compound. Analogously, virtually any electrophilic group can be used to functionalize the hydrophobic portion of the amphiphilic compound, so long as reaction can take place with the nucleophilic group on the surface of the bioabsorbable polymeric substrate. In embodiments, the reaction occurs without need for catalysts, ultraviolet or other radiation. In embodiments, the reactions the complementary members should be complete in under 60 minutes, in embodiments under 30 minutes, in yet other embodiments, the reaction occurs in about 5 to 15 minutes or less.

Non-limiting examples of nucleophilic groups include, but are not limited to, $-NH_2$, $-NHR$, $-N(R)_2$, $-SH$, $-OH$, $-COOH$, $-C_6H_4-OH$, $-PH_2$, $-PHR$, $-P(R)_2$, $-NH-NH_2$, $-CO-NH-NH_2$, $-C_5H_4N$, etc. wherein R is hydrocarbyl, typically $C_1$-$C_4$ alkyl or monocyclic aryl. Organometallic moieties are also useful nucleophilic groups for the purposes of this disclosure, particularly those that act as carbanion donors. Examples of organometallic moieties include: Grignard functionalities —RMgHal wherein R is a carbon atom (substituted or unsubstituted), and Hal is halo, typically bromo, iodo or chloro; and lithium-containing functionalities, typically alkyllithium groups; sodium-containing functionalities.

It will be appreciated by those of ordinary skill in the art that certain nucleophilic groups must be activated with a base so as to be capable of reaction with an electrophile. For example, when there are nucleophilic sulfhydryl and hydroxyl groups on the surface of the bioabsorbable polymeric substrate, the composition must be admixed with an aqueous base in order to remove a proton and provide an $-S^-$ or $-O^-$ species to enable reaction with an electrophile. Unless it is desirable for the base to participate in the reaction, a non-nucleophilic base is used. In some embodiments, the base may be present as a component of a buffer solution.

The selection of electrophilic groups provided on the hydrophobic portion of the amphiphilic compound is made so that reaction is possible with the specific nucleophilic groups on the surface of the bioabsorbable polymeric substrate. Thus, when the surface of the bioabsorbable polymeric substrate is functionalized with amino groups, the hydrophobic portion of the amphiphilic compound is functionalized with groups selected so as to react with amino groups. Analogously, when the surface of the bioabsorbable polymeric substrate is functionalized with sulhydryl moieties, the corresponding electrophilic groups are sulfhydryl-reactive groups, and the like.

By way of example, when the surface of the bioabsorbable polymeric substrate is functionalized with amino groups (generally although not necessarily primary amino groups), the electrophilic groups present on the hydrophobic portion of the amphiphilic compound are amino reactive groups such as, but not limited to: (1) carboxylic acid esters, including cyclic esters and "activated" esters; (2) acid chloride groups (—CO—Cl); (3) anhydrides (—(CO)—O—(CO)—R); (4) ketones and aldehydes, including α,β-unsaturated aldehydes and ketones such as —CH=CH—CH=O and —CH=CH—C(CH$_3$)=O; (5) halides; (6) isocyanate (—N=C=O); (7) isothiocyanate (—N=C=S); (8) epoxides; (9) activated hydroxyl groups (e.g., activated with conventional activating agents such as carbonyldiimidazole or sulfonyl chloride); and (10) olefins, including conjugated olefins, such as ethenesulfonyl (—SO$_2$CH=CH$_2$) and analogous functional groups, including acrylate (—CO$_2$—C=CH$_2$), methacrylate (—CO$_2$—C(CH$_3$)=CH$_2$)), ethyl acrylate (—CO$_2$—C(CH$_2$CH$_3$)=CH$_2$), and ethyleneimino (—CH=CH—C=NH). Since a carboxylic acid group per se is not susceptible to reaction with a nucleophilic amine, components containing carboxylic acid groups must be activated so as to be amine-reactive. Activation may be accomplished in a variety of ways, but often involves reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxy-succinimide or N-hydroxysulfosuccinimide in the presence of DCC to form reactive electrophilic groups, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride group. In a further example, a carboxylic acid may be converted to an acid chloride group using, e.g., thionyl chloride or an acyl chloride capable of an exchange reaction. Specific reagents and procedures used to carry out such activation reactions will be known to those of ordinary skill in the art and are described in the pertinent texts and literature.

Analogously, when the surface of the bioabsorbable polymeric substrate is functionalized with sulfhydryl, the electrophilic groups present on the hydrophobic portion of the amphiphilic compound are groups that react with a sulfhydryl moiety. Such reactive groups include those that form thioester linkages upon reaction with a sulfhydryl group, such as those described in PCT Publication No. WO 00/62827 to Wallace et al. As explained in detail therein, such "sulfhydryl reactive" groups include, but are not limited to: mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarinide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; and isocyanates. With these sulfhydryl reactive groups, auxiliary reagents can also be used to facilitate bond formation, e.g., 1-ethyl-3-[3-dimethylaminopropyl]carbodiimide can be used to facilitate coupling of sulfhydryl groups to carboxyl-containing groups.

In addition to the sulfhydryl reactive groups that form thioester linkages, various other sulfydryl reactive functionalities can be utilized that form other types of linkages. For example, compounds that contain methyl imidate derivatives form imido-thioester linkages with sulfhydryl groups. Alternatively, sulfhydryl reactive groups can be employed that form disulfide bonds with sulfhydryl groups, such groups generally have the structure —S—S—Ar where Ar is a substituted or unsubstituted nitrogen-containing heteroaromatic moiety or a non-heterocyclic aromatic group substituted with an electron-withdrawing moiety, such that Ar may be, for example, 4-pyridinyl, o-nitrophenyl, m-nitrophenyl, p-nitrophenyl, 2,4-dinitrophenyl, 2-nitro-4-benzoic acid, 2-nitro-4-pyridinyl, etc. In such instances, auxiliary reagents, e.g., mild oxidizing agents such as hydrogen peroxide, can be used to facilitate disulfide bond formation.

Yet another class of sulfhydryl reactive groups forms thioether bonds with sulfhydryl groups. Such groups include, inter alia, maleimido, substituted maleimido, haloalkyl, epoxy, imino, and aziridino, as well as olefins (including conjugated olefins) such as ethenesulfonyl, etheneimino, acrylate, methacrylate, and α,β-unsaturated aldehydes and ketones.

When the surface of the bioabsorbable polymeric substrate is functionalized with —OH, the electrophilic functional groups on the hydrophobic portion of the amphiphilic compound must react with hydroxyl groups. The hydroxyl group may be activated as described above with respect to carboxylic acid groups, or it may react directly in the presence of base with a sufficiently reactive electrophile such as an epoxide group, an aziridine group, an acyl halide, or an anhydride.

When the surface of the bioabsorbable polymeric substrate is functionalized with an organometallic nucleophile such as a Grignard functionality or an alkyllithium group, suitable electrophilic functional groups for reaction therewith are those containing carbonyl groups, including, by way of example, ketones and aldehydes.

It will also be appreciated that certain functional groups can react as nucleophiles or as electrophiles, depending on the selected reaction partner and/or the reaction conditions. For example, a carboxylic acid group can act as a nucleophile in the presence of a fairly strong base, but generally acts as an electrophile allowing nucleophilic attack at the carbonyl carbon and concomitant replacement of the hydroxyl group with the incoming nucleophile.

Table 1, below illustrates, solely by way of example, representative complementary pairs of electrophilic and nucleophilic functional groups that may be employed in functionalizing the bioabsorbable polymeric substrate (e.g., $R_1$ in Table 1) and the hydrophobic portion of the amphiphilic compound (e.g., $R_2$ in Table 1).

TABLE 1

| REPRESENTATIVE NUCLEOPHILIC COMPONENT (A, $FN_{NU}$) | REPRESENTATIVE ELECTROPHILIC COMPONENT (B, $FN_{EL}$) | RESULTING LINKAGE |
|---|---|---|
| $R^1$—NH$_2$ | $R^2$—O—(CO)—O—N(COCH$_2$) (succinimidyl carbonate terminus) | $R^1$—NH—(CO)—O—$R^2$ |

TABLE 1-continued

| REPRESENTATIVE NUCLEOPHILIC COMPONENT (A, $FN_{NU}$) | REPRESENTATIVE ELECTROPHILIC COMPONENT (B, $FN_{EL}$) | RESULTING LINKAGE |
|---|---|---|
| $R^1$—SH | $R^2$—O—(CO)—O—N(COCH$_2$) | $R^1$—S—(CO)—O—$R^2$ |
| $R^1$—OH | $R^2$—O—(CO)—O—N(COCH$_2$) | $R^1$—S—(CO)—$R^2$ |
| $R^1$—NH$_2$ | $R^2$—O(CO)—CH=CH$_2$ (acrylate terminus) | $R^1$—NH—CH$_2$CH$_2$—(CO)—O—$R^2$ |
| $R^1$—SH | $R^2$—O—(CO)—CH=CH$_2$ | $R^1$—S—CH$_2$CH$_2$—(CO)—O—$R^2$ |
| $R^1$—OH | $R^2$—O—(CO)—CH=CH$_2$ | $R^1$—O—CH$_2$CH$_2$—(CO)—O—$R^2$ |
| $R^1$—NH$_2$ | $R^2$—O(CO)—(CH$_2$)$_3$—CO$_2$N(COCH$_2$) (succinimidyl glutarate terminus) | $R^1$—NH—(CO)—(CH$_2$)$_3$—(CO)—O$R^2$ |
| $R^1$—SH | $R^2$—O(CO)—(CH$_2$)$_3$—CO$_2$—N(COCH$_2$) | $R^1$—S—(CO)—(CH$_2$)$_3$—(CO)—O$R^2$ |
| $R^1$—OH | $R^2$—O(CO)—(CH$_2$)$_3$—CO$_2$—N(COCH$_2$) | $R^1$—O—(CO)—(CH$_2$)$_3$—(CO)—O$R^2$ |
| $R^1$—NH$_2$ | $R^2$—O—CH$_2$—CO$_2$—N(COCH$_2$) (succinimidyl acetate terminus) | $R^1$—NH—(CO)—CH$_2$—O$R^2$ |
| $R^1$—SH | $R^2$—O—CH$_2$—CO$_2$—N(COCH$_2$) | $R^1$—S—(CO)—CH$_2$—O$R^2$ |
| $R^1$—OH | $R^2$—O—CH$_2$—CO$_2$—N(COCH$_2$) | $R^1$—O—(CO)—CH$_2$—O$R^2$ |
| $R^1$—NH$_2$ | $R^2$—O—NH(CO)—(CH$_2$)$_2$—CO$_2$—N(COCH$_2$) (succinimidyl succinamide terminus) | $R^1$—NH—(CO)—(CH$_2$)$_2$—(CO)—NH—O$R^2$ |
| $R^1$—SH | $R^2$—O—NH(CO)—(CH$_2$)$_2$—CO$_2$—N(COCH$_2$) | $R^1$—S—(CO)—(CH$_2$)$_2$—(CO)—NH—O$R^2$ |
| $R^1$—OH | $R^2$—O—NH(CO)—(CH$_2$)$_2$—CO$_2$—N(COCH$_2$) | $R^1$—O—(CO)—(CH$_2$)$_2$—(CO)—NH—O$R^2$ |
| $R^1$—NH$_2$ | $R^2$—O—(CH$_2$)$_2$—CHO (propionaldehyde terminus) | $R^1$—NH—(CO)—(CH$_2$)$_2$—O$R^2$ |
| $R^1$—NH$_2$ | 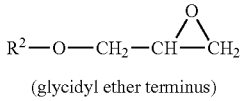 $R^2$—O—CH$_2$—CH—CH$_2$ (with epoxide O) (glycidyl ether terminus) | $R^1$—NH—CH$_2$—CH(OH)—CH$_2$—O$R^2$ and $R^1$—N[CH$_2$—CH(OH)—CH$_2$—O$R^2$]$_2$ |
| $R^1$—NH$_2$ | $R^2$—O—(CH$_2$)$_2$—N=C=O (isocyanate terminus) | $R^1$—NH—(CO)—NH—CH$_2$—O$R^2$ |
| $R^1$—NH$_2$ | $R^2$—SO$_2$—CH=CH$_2$ (vinyl sulfone terminus) | $R^1$—NH—CH$_2$CH$_2$—SO$_2$—$R^2$ |
| $R^1$—SH | $R^2$—SO$_2$—CH=CH$_2$ | $R^1$—S—CH$_2$CH$_2$—SO$_2$—$R^2$ |

In embodiments, the surface of the bioabsorbable polymeric substrate is functionalized with a first click-reactive member and the hydrophobic portion of the amphiphilic compound is functionalized with a second click-reactive member complementary to the first click-reactive member. The "click-reactive members" are meant to include those reactive members used in the processes known to those skilled in the art as Click chemistry.

Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C—N triple bonds and C—C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkyl/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO (difluorinated cyclooctyne) and DIMAC (6,7-dimethoxyazacyclooct-4-yne). Reaction of the alkynes and azides is very specific and essentially inert against the chemical environment of biological tissues. One reaction scheme may be represented as:

a) 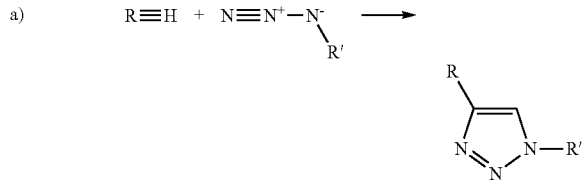

where R and R' are a polymeric substrate or an amphiphilic compound.

The Diels-Alder reaction combines a diene (a molecule with two alternating double bonds) and a dienophile (an alkene) to make rings and bicyclic compounds. Examples include:

Dienes

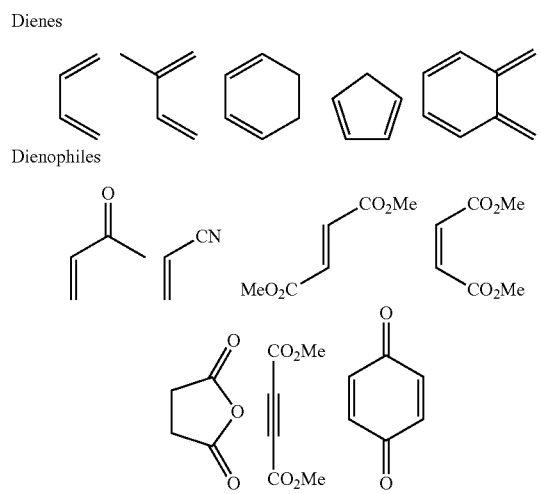

Dienophiles

The thiol-alkene (thiol-ene) reaction is a hydrothiolation, i.e., addition of RS—H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

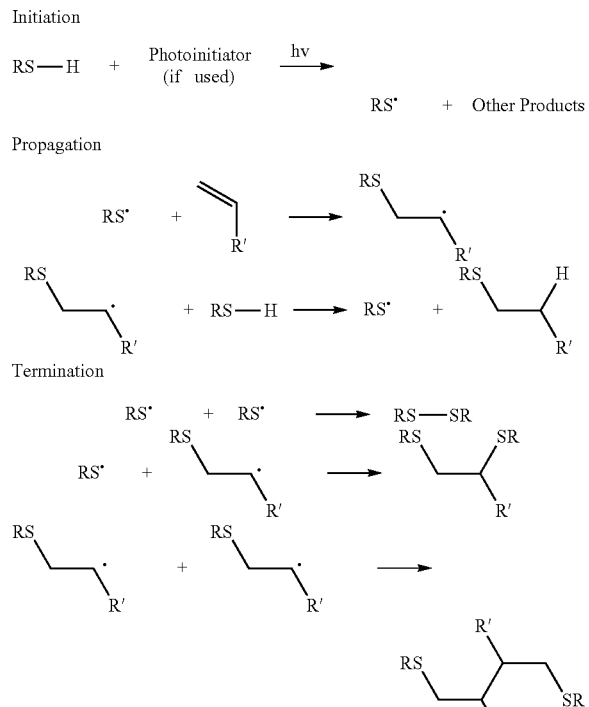

In embodiments, the surface of the bioabsorbable polymeric substrate and the hydrophobic portion of the amphiphilic compound are functionalized to include a first click-reactive member which is an alkyne and a second click-reactive member which is an azide, respectively. In embodiments, the surface of the bioabsorbable polymeric substrate and the hydrophobic portion of the amphiphilic compound are functionalized to include a first click-reactive member which includes an azide group and a second click-reactive member which is an alkene, respectively. In yet other embodiments, the surface of the bioabsorbable polymeric substrate and the hydrophobic portion of the amphiphilic compound are functionalized to include a first click-reactive member that includes a third group and a second click-reactive member that is an alkene, respectively.

The first and second click-reactive members are intended to react and covalently bond the amphiphilic compound to the functionalized surface of the bioabsorbable polymeric substrate at a physiologic pH. However, in some embodiments, the first and second click-reactive members may react quicker or more completely following the addition of a catalyst, such as a pH modifier, a metal ion catalyst or the introduction of heat or radiation. In embodiments, the addition of UV radiation may enhance the formation of a covalent bond between the first and second click-reactive members. In embodiments, the addition of a metal catalyst, e.g., transition metal ions such as copper ions, may assist with the formation of a covalent bond between the first and second click-reactive members.

Figure 3:
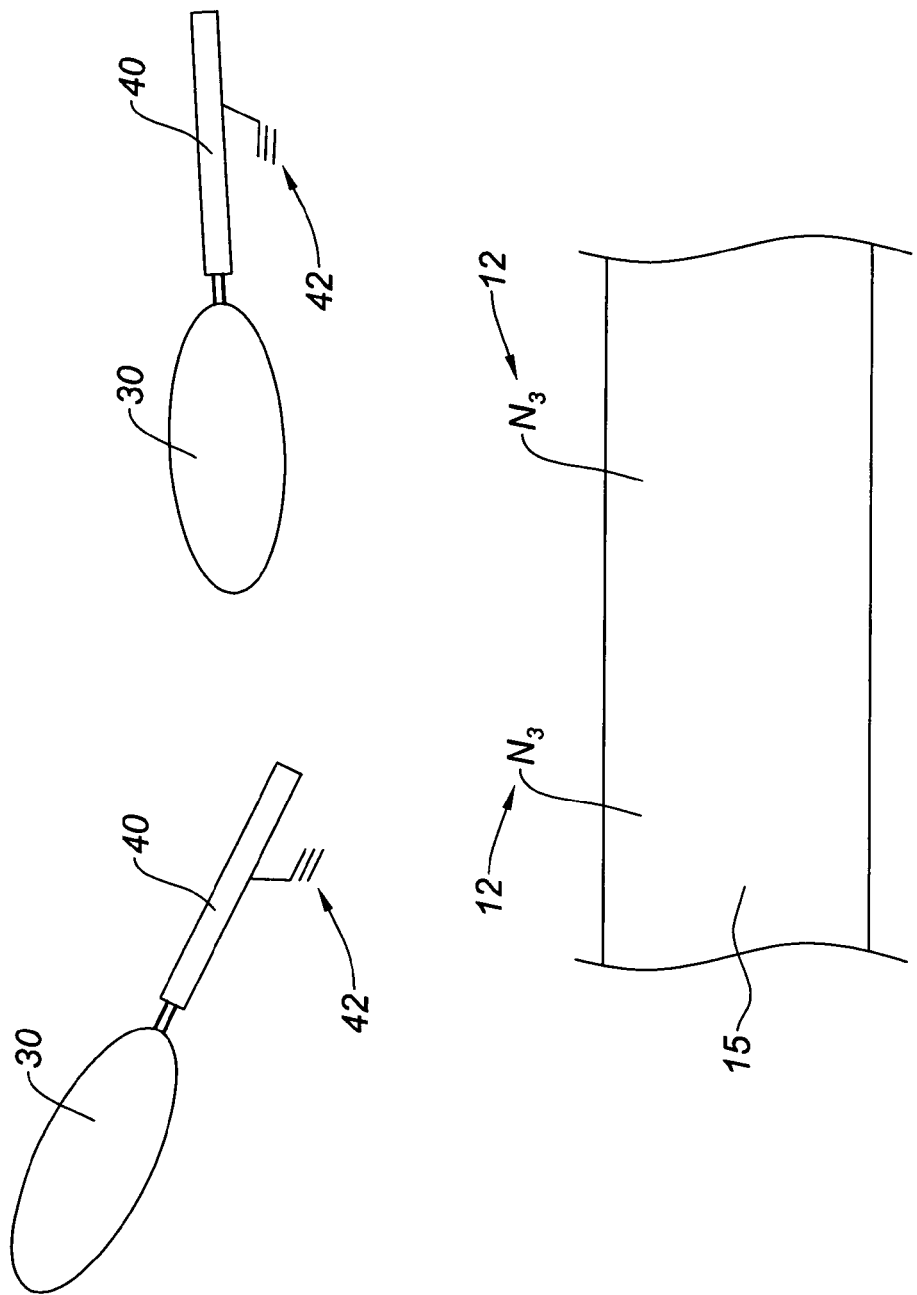
FIG. 3 schematically illustrates a medical device having an activated surface and an activated amphiphilic compound.

As shown in FIG. 3, bioabsorbable polymeric substrate 15 includes first reactive functional members, in this case azide groups 12. An amphiphilic compound having hydrophilic portion 30 and hydrophobic portion 40 wherein hydrophobic portion 40 includes second reactive members, in this case alkyne groups 42 are contacted with substrate 15 in solution under suitable reaction conditions. As those skilled in the art will recognize, reaction times between the azide and alkyne members can be reduced from about 24 hours at room temperature to mere seconds at room temperature by the presence of transition metal ions, such as copper ions.

Figure 4:
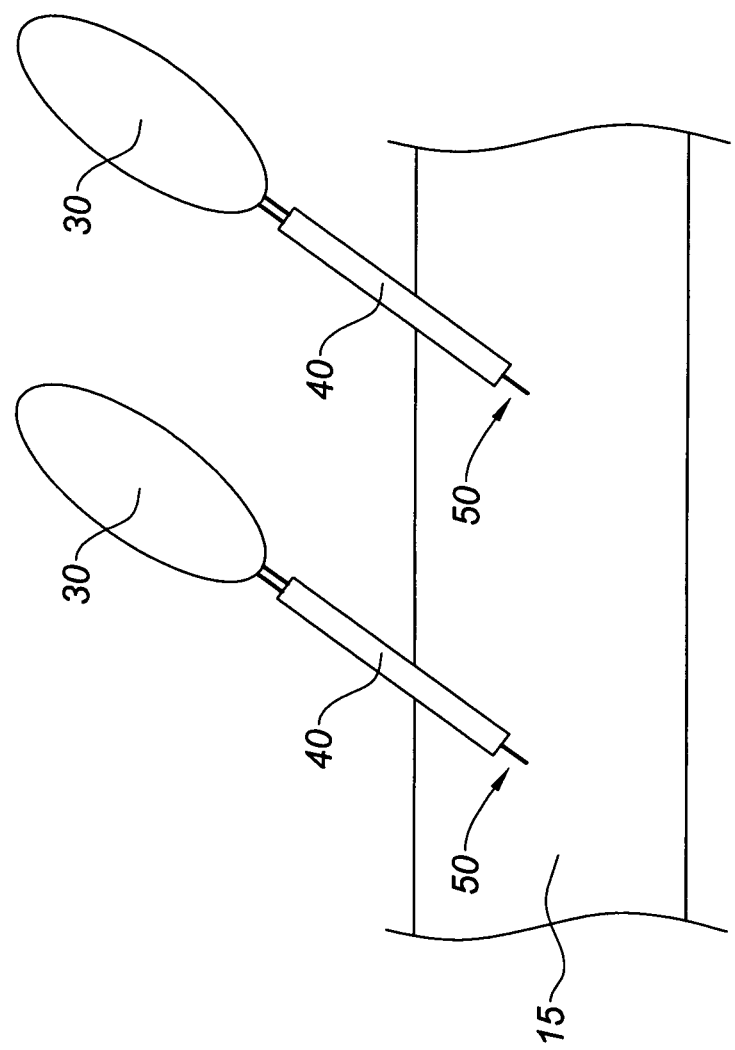
FIG. 4 schematically illustrates the medical device shown in FIG. 3 having the amphiphilic compound covalently bonded thereto.

As shown in FIG. 4, after reaction, bioabsorbable polymeric substrate 15 includes a coating of the amphiphilic compound having hydrophilic portion 30 extending away from substrate 15 and hydrophobic portion 40 covalently bound to substrate 15 via a triazole linkage 50.

Functionalizing the Substrate and Amphiphilic Compound

The first and second reactive members may be positioned on the bioabsorbable polymeric substrate and amphiphilic compound using any variety of suitable chemical processes. With respect to the first reactive members on the bioabsorbable polymeric substrate, it is contemplated that a plurality of first reactive members may be present and may be terminally located, or alternatively located along the length of the polymer chain.

For example, the monomers from which the bioabsorbable polymeric substrate is made can be functionalized so that the reactive members appear along the length of the bioabsorbable polymer. In such embodiments, the monomers can be initially functionalized with a member such as a halogen to provide a reactive site at which the desired first reactive member can be attached after polymerization. Thus, for example, a cyclic lactone (e.g., glycolide, lactide, caprolactone, etc.) can be halogenated and then polymerized using known techniques for ring opening polymerization. Once polymerized, the halogenated sites along the resulting polyester chain can be functionalized with the first reactive member. For example, the halogenated polyester can be reacted with sodium azide to provide azide groups along the polymer chain or with propagyl alcohol to provide alkyne groups along the polymer chain. See, R. Riva et al., *Polymer* 49, pages 2023-

2028 (2008) for a description of such reaction schemes. In another example, a propargyl group may be introduce into a cyclic carbonate monomer to form 5-methyl-5-propargyloxycarbonyl-1,3-dioxan-2-one (MPC) which is polymerizable with lactide to form p(LA-co-MPC). See, Q. Shi et al., *Biomaterials*, 29, pages 1118-1126 (2008). Alternatively, a preformed biodegradable polyester can be halogenated by reaction with a non-nucleophilic strong base, such as lithium diisopropylamide, followed by electrophilic substitution with iodine chloride. The halogenated polyester is then reacted with sodium azide or propagyl alcohol to provide azide or alkyne groups, respectively. Other methods for functionalizing lactones are described in Jerome et al., *Advanced Drug Delivery Reviews*, 60, pages 1056-1076 (2008). The entire disclosure of each of these articles is incorporated herein by this reference.

In other embodiments, the bioabsorbable polymeric substrate is functionalized after it has been fabricated into the desired form. For example, bioabsorbable polymeric fibers can be functionalized after the spinning process. In embodiments, the fibers are surface treated and then activated with the first reactive member (optionally with a coupling agent (e.g., a silane coupling agent) being used). Surface activation of bioabsorbable and biocompatible aliphatic polyesters can be achieved by acid or base hydrolysis, treatment by means of cold plasma, by chemical reactions or electromagnetic radiations. It is contemplated that such surface activation can be performed before or after the fibers are made into a textile structure.

Hydrolysis can be conducted in the presence of an aqueous solution of a base or an acid to accelerate surface reaction, inasmuch as excessively long processes of activation can induce a reduction in molecular weight and thus in the mechanical properties of the material. Suitable bases for obtaining watery solutions suited to the aim are, for example, strong alkalis, such as LiOH, $Ba(OH)_2$, $Mg(OH)_2$, NaOH, KOH, $Na_2CO_3$, $Ca(OH)_2$ and the weak bases, such as for example $NH_4OH$ and the amines such as methylamine, ethylamine, diethylamine and dimethylamine. Acids suitable for surface hydrolysis treatments can be chosen, for example, from among HCl, $HClO_3$, $HClO_4$, $H_2SO_3$, $H_2SO_4$, $H_3PO_3$, $H_3PO_4$, HI, $HIO_3$, HBr, lactic acid, glicolic acid. Surface activation by means of hydrolysis can be conducted at temperatures preferably comprised between 0 degrees Celsius and the material softening temperature. Plasma treatment can be carried out both in the presence of a reactive gas, for example air, Ar, $O_2$ with the formation of surface activation of oxygenate type, such as —OH, —CHO, —COOH.

Surface treatment, whether hydrolytic or with plasma, can remain unaltered or can be followed by further chemical modifications to provide the first reactive members on the bioabsorbable polymeric substrate. Thus, for example, the COONa members generated by a base hydrolysis can be subsequently converted into COOH members by treatment with strong mineral acids. Further, the surface freeing of alcoholic members by means of a hydrolysis process can be followed by reaction by means of the addition of a compound provided with functional group or groups able to react with surface alcoholic groups, such as for example by means of the addition of an anhydride such as succinic anhydride, with the conversion of —OH groups into —O—CO—$CH_2$—$CH_2$—COOH groups. Suitable surface activation techniques are disclosed in U.S. Pat. No. 6,107,453, the entire disclosure of which is incorporated herein by this reference.

With respect to the hydrophobic portion of the amphiphilic compound, it is contemplated that one or more than one second reactive members can be provided thereon. The process used to incorporate the second reactive members on the hydrophobic portion of the amphiphilic compound will be chosen based upon the nature of the hydrophobic portion.

For example, where the hydrophobic portion is based on a fatty acid, the second reactive members can be attached using the following synthetic route:

Scheme 1. Synthetic Route to Head Group Azide-Tagged Diacylglyerol Scaffold 2

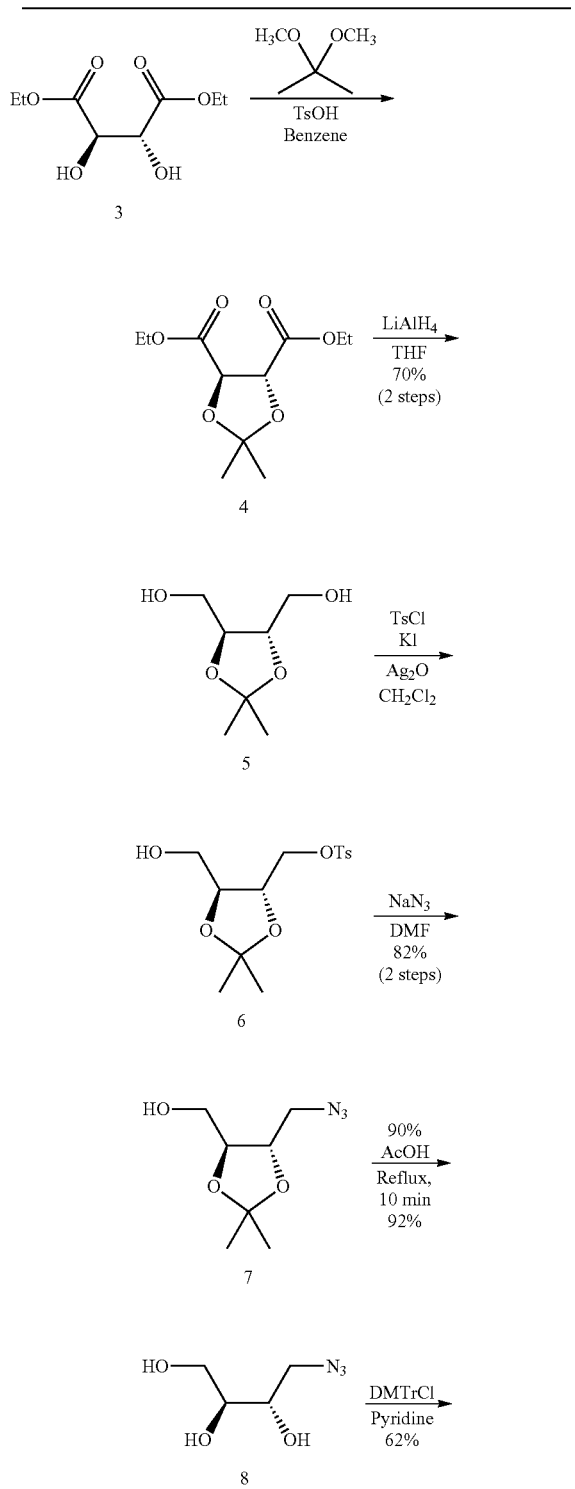

15

-continued

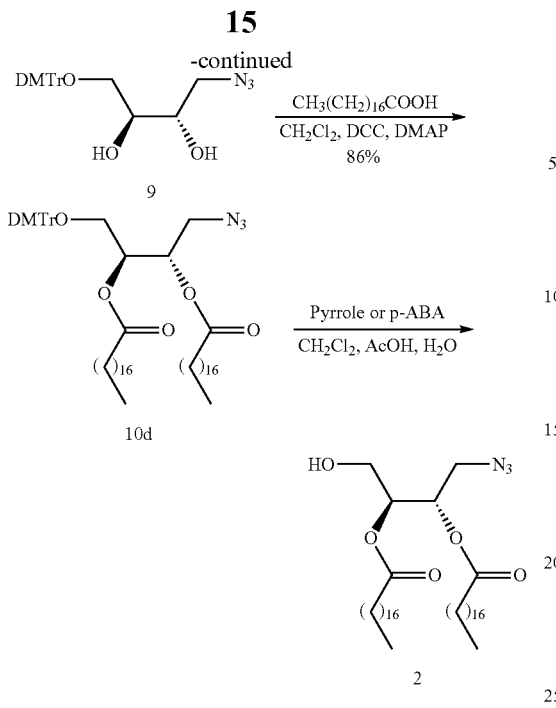

In embodiments, the acids used to introduce the acyl chains (10d) may be dicarboxylic acid fatty acids which provide for the synthesis of di-azide compounds.

In other embodiments where the hydrophobic portion is based on a hydrophobic peptide, N-propargyl maleimide can be used to attach alkyne group (the second reactive members) on to the protein using to the thiol group as shown below:

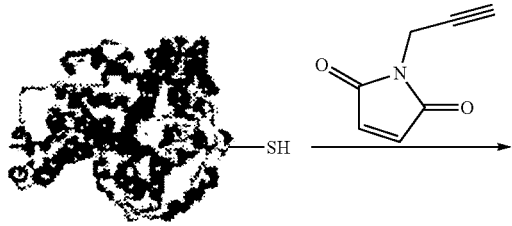

16

-continued

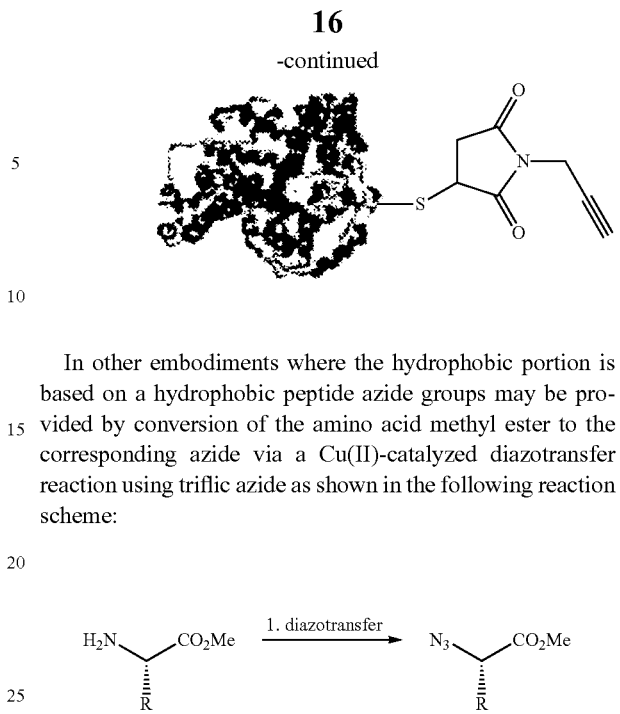

In other embodiments where the hydrophobic portion is based on a hydrophobic peptide azide groups may be provided by conversion of the amino acid methyl ester to the corresponding azide via a Cu(II)-catalyzed diazotransfer reaction using triflic azide as shown in the following reaction scheme:

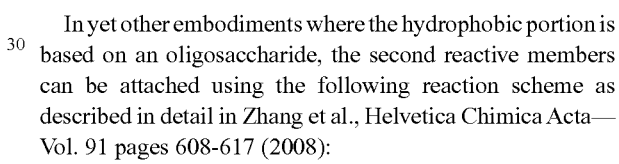

In yet other embodiments where the hydrophobic portion is based on an oligosaccharide, the second reactive members can be attached using the following reaction scheme as described in detail in Zhang et al., Helvetica Chimica Acta—Vol. 91 pages 608-617 (2008):

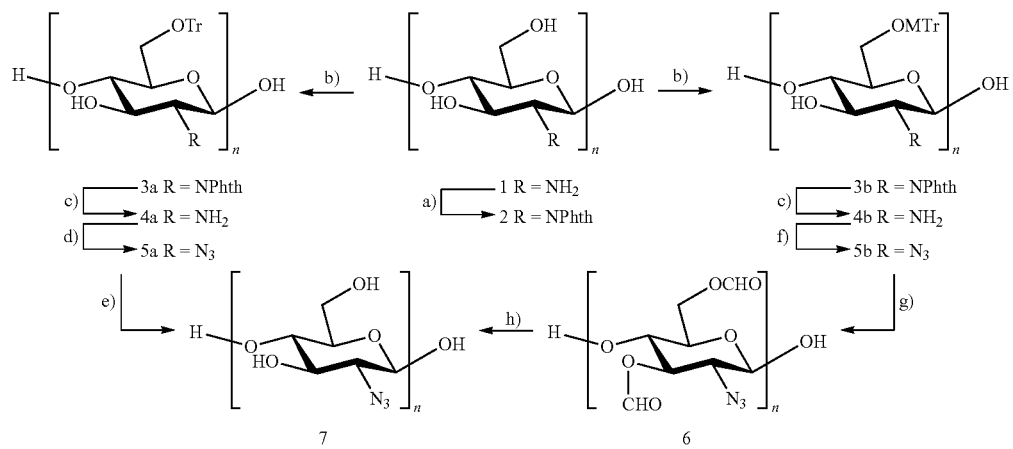

In embodiments, a plurality of different reactive members may be positioned on each of the bioabsorbable polymeric substrate and amphiphilic compound.

Various modifications and variations of the polymers, amphiphilic compounds, medical devices, click-reactive members and processes described herein will be apparent to those skilled in the art from the foregoing detailed description. Such modifications and variations are intended to come within the scope of the following claims.

What is claimed is:

1. A medical device comprising:
a bioabsorbable polymeric substrate having a coating, the coating comprising an amphiphilic compound having a hydrophilic portion and hydrophobic portion, the hydrophobic portion of the amphiphilic compound being covalently bonded to the bioabsorbable polymeric substrate, wherein the hydrophilic portion is derived from a chitosan oligomer having a low degree of acetylation, ranging from about 0 to about 30%, and the hydrophobic portion is derived from a chitosan oligomer having a higher degree of acetylation, greater than about 50% at a pH<6.

2. A medical device comprising:
a bioabsorbable polymeric substrate having a coating, the coating comprising an amphiphilic compound having a hydrophilic portion and hydrophobic portion, the hydrophobic portion of the amphiphilic compound being covalently bonded to the bioabsorbable polymeric substrate, wherein the hydrophobic portion is derived from a chitosan oligomer having a low degree of acetylation, ranging from about 0 to about 10%, and the hydrophilic portion is derived from a hyaluronic acid oligomer or alginate oligomer which under pH>7 conditions displays a negative charge.

3. The medical device of claim 1 wherein the hydrophilic portion of the amphiphilic compound favors cellular attachment.

4. The medical device of claim 1 wherein the hydrophobic portion of the amphiphilic compound provides a barrier thereby retarding the degradation of the medical device.

5. The medical device of claim 1 wherein the bioabsorbable polymeric substrate includes a first reactive member attached thereto and the hydrophobic portion of the amphiphilic compound is functionalized with a second complimentary reactive member attached thereto, the first reactive member and second complimentary reactive member being able to interact together to covalently bond the hydrophobic portion of the amphiphilic compound to the bioabsorbable polymeric substrate.

6. The medical device of claim 5, wherein the first reactive member comprises a click-reactive member and the second complimentary reactive member comprises a complimentary click-reactive member.

7. The medical device of claim 5, wherein the first reactive member is a nucleophilic functional group and the second complimentary reactive member is an electrophilic functional group.

8. The medical device of claim 5, wherein said first and second reactive members are able to interact together according to a reaction selected from the group consisting in Huisgen cycloaddition, Diels-Alder reactions, thiol-alkene reactions and maleimide-thiol reactions.

9. The medical device of claim 5, wherein the first reactive member is an alkyne and the second complimentary reactive member is an azide.

10. The medical device of claim 5, wherein the first reactive member is an azide and the second complimentary reactive member is an alkyne.

11. The medical device according to claim 5, wherein the first reactive member is an azide and the second complimentary reactive member is an alkene.

12. The medical device of claim 2 wherein the hydrophilic portion of the amphiphilic compound favors cellular attachment.

13. The medical device of claim 2 wherein the hydrophobic portion of the amphiphilic compound provides a barrier thereby retarding the degradation of the medical device.

14. The medical device of claim 2 wherein the bioabsorbable polymeric substrate includes a first reactive member attached thereto and the hydrophobic portion of the amphiphilic compound is functionalized with a second complimentary reactive member attached thereto, the first reactive member and second complimentary reactive member being able to interact together to covalently bond the hydrophobic portion of the amphiphilic compound to the bioabsorbable polymeric substrate.

15. The medical device of claim 14, wherein the first reactive member comprises a click-reactive member and the second complimentary reactive member comprises a complimentary click-reactive member.

16. The medical device of claim 14, wherein the first reactive member is a nucleophilic functional group and the second complimentary reactive member is an electrophilic functional group.

17. The medical device of claim 14, wherein said first and second reactive members are able to interact together according to a reaction selected from the group consisting in Huisgen cycloaddition, Diels-Alder reactions, thiol-alkene reactions and maleimide-thiol reactions.

18. The medical device of claim 14, wherein the first reactive member is an alkyne and the second complimentary reactive member is an azide.

19. The medical device of claim 14, wherein the first reactive member is an azide and the second complimentary reactive member is an alkyne.

20. The medical device according to claim 14, wherein the first reactive member is an azide and the second complimentary reactive member is an alkene.

* * * * *